US005166535A

United States Patent [19]

Takahashi

[11] Patent Number: 5,166,535

[45] Date of Patent: Nov. 24, 1992

[54] SURFACE INSPECTING APPARATUS WITH SURFACE INSPECTION WIDTH ADJUSTMENT

[75] Inventor: Ippei Takahashi, Minami-ashigara, Japan

[73] Assignee: Fuji Photo Film Co., Ltd., Kanagawa, Japan

[21] Appl. No.: 599,161

[22] Filed: Oct. 17, 1990

[30] Foreign Application Priority Data

Oct. 19, 1989 [JP] Japan ........ 1-271989

[51] Int. Cl.[5] ........ G01N 21/88; H01J 3/14

[52] U.S. Cl. ........ 250/563; 250/560; 250/236; 356/431

[58] Field of Search ........ 250/563, 562, 571, 572, 250/560, 561, 235, 236; 356/430, 431

[56] References Cited

U.S. PATENT DOCUMENTS 3,646,353 2/1972 Bhullar et al. ........ 250/563
4,173,441 11/1979 Wolf ........ 250/563
4,205,769 6/1980 Blitchington ........ 250/563
4,211,132 7/1980 Nichols, III et al. ........ 250/563
4,247,204 1/1981 Merlen et al. ........ 250/563
4,538,915 9/1985 Faulhaber ........ 250/563
4,791,304 12/1988 Iida ........ 250/563
4,868,403 1/1989 Takahashi et al. ........ 250/563

*Primary Examiner*—David C. Nelms
*Assistant Examiner*—Michael Messinger
*Attorney, Agent, or Firm*—Sughrue, Mion, Zinn, Macpeak & Seas

[57] ABSTRACT

A surface inspecting apparatus generates an inspecting width gate signal by in a procedure wherein when the subject matter is subjected to the scanning via the light beam, a counting means digitizes the detected position of both the front and rear ends of the subject and then an operating means calculates values which indicate the positions included within the range between both of the ends, thus generating the inspecting width gate signal. Consequently, it is possible to inspect any subject matter without manually resetting the effective inspecting range whenever a subject matter changes in width.

10 Claims, 8 Drawing Sheets

SURFACE INSPECTING APPARATUS WITH SURFACE INSPECTION WIDTH ADJUSTMENT

BACKGROUND OF THE INVENTION

1. Field of the Invention

This invention relates to a surface inspecting apparatus, and more particularly, to a flying spot type surface inspecting apparatus which inspects defects existing on a suface of a subject matter to be inspected such as a film, a paper, iron or the like by using a light beam.

2. Description of the Related Art

A conventional flying spot type surface inspecting apparatus comprises a scanner which includes a laser beam source irradiating a light beam, a lens system, a rotating mirror and the like, a light receiver receiving transmitted light or reflected light from the subject matter being inspected, and a processing circuit which discriminates the presence of a defect by making use of photoelectric conversion signals obtained from the light receiver. FIG. 1 shows an example of the surface inspecting apparatus above-mentioned.

In FIG. 1, a scanning light beam 11, which is irradiated from a scanner 10, traces a scanning line 12*a* on the surface of a subject matter 12 moving in an X-direction. After being reflected on the surface of the subject matter 12 in the position of the scanning line 12*a*, the light beam 11 enters a light detector 13 to be photoelectrically converted. The electric signal outputted from the light detector 13 is subjected to the waveform shaping in a filtering circuit 14 so as to intensify a portion having a defect. The signals are classified by a threshold level in a binarizing circuit 16 into two classifications. For example, the signal over a threshold level is allotted to "1" as a defect signal and the signal under a threshold level is allotted to "0" as a normal signal.

On the other hand, a photosensor 17 installed together with the scanner 10 receives the initial light beam 11 of every scanning and electrically converts the received light beam 11 into an electric signal to be outputted. When the electric signal is given, a counter 18 starts to count a number of reference pulses having a sufficiently-short and a constant cycle formed in a reference pulse generator 19. A comparing circuit 22 outputs "0" until the counting number increases from zero to a predetermined value (which corresponds to a starting position $K_1$ preset by means of a starting position preset circuit 21) while another comparing circuit 23 outputs "1". When the counting number exceeds the predetermined value corresponding to the starting position $K_1$ which is set in advance, the comparing circuit 22 changes its value from "0" to "1" and maintains the new value. By this, an AND circuit 24 continues outputting "1". Sequentially, when the counting number of the reference pulse gets over another predetermined value which corresponds to an ending position $K_2$ preset by means of an ending position preset circuit 26, the comparing circuit 23 changes its output value from "1" to "0". Thereafter, the AND circuit 24 maintain the new value "0".

As described above, an inspecting width gate circuit 27 which is enclosed with a broken line outputs an inspecting width gate signal E as shown in FIG. 2E. Therefore, only when the aforementioned binarizing circuit 16 outputs a defect signal "1", all of the signals to be inputted into the AND circuit 27 become "1", and thereby the AND circuit 27 is to output a digital signal "1" which corresponds to a defect detecting signal F as shown in FIG. 2F.

FIGS. 2A to 2F show waveforms of the signals A to F corresponding to their respective portions in the processing circuit shown in FIG. 1. In these figures, when an effective inspecting range in the direction of the scanning is defined narrower than the width of the subject matter 12 by determining the values $K_1$ and $K_2$ to be preset, it is possible to continuously inspect the subject matter 12 skipping the edge portions thereof. This enables the defect detecting signal F to be detected separately from the noise made by the edges of the subject matter 12 shown in FIG. 2C.

In the conventional surface inspecting apparatus described above, the starting point and the ending point of the effective inspection need be manually set up by means of switches or the like so that the counter 18 may count up the reference clock in order to define the gate signal between the start setting point $K_1$ and the end setting point $K_2$. Therefore, the conventional method has a disadvantage in that the set-up for the starting point and the ending point must be changed whenever the width of the subject matter changes.

SUMMARY OF THE INVENTION

This invention has been accomplished in view of what is discussed above. The object of this invention is, therefore to provide a surface inspecting apparatus wherein the effective inspecting range need not be set or reset manually by the switches or the like whenever the subject matter changes in its width.

According to one aspect of this invention, for achieving the objects described above, there is provided a surface inspecting apparatus wherein a subject matter is inspected for detecting defects on a surface thereof by means of a scanner scanning and irradiating a light beam on the subject matter being conveyed, which comprises a light detecting means irradiating the light beam once before the starting of every scanning; a light receiving means receiving a reflected light of the light beam irradiated on the subject matter; a first counting means counts the interval from when the light detecting means detects the light beam until said light receiving means detects the front end of the subject matter; a second counting means making a count in the interval from when said light detecting means detects said light beam until said light receiving means detects the rear end of the subject matter; an operating means calculating a value which is larger than the value counted via said first counting means by a predetermined amount, as well as a value which is smaller than the value counted via the second counting means by a predetermined amount; and a gate signal generating means which, according to two resultant values calculated by said operating means, generates a gate signal by adopting the time when the light detecting means detects the light beam as a reference point of counting, in order to select an effective portion out of the reflected light signal obtained via said light receiving means.

According to another aspect of this invention, there is provided a surface inspecting apparatus wherein a subject matter is inspected for detecting defects on a surface thereof by means of a scanner scanning and irradiating a light beam on the subject matter being conveyed, which comprises a light detecting means irradiating the light beam once before the starting of every scanning; a light receiving means receiving the reflected light of the light beam irradiated on the subject matter;

a counting means making a count during the interval from when the light receiving means detects the front end of the subject matter until said light receiving means detects the rear end of the subject matter; an operating means for calculating a value which is smaller than the value counted via the counting means by a predetermined amount; and a gate signal generating means which generates a gate signal, by adopting the time when the light receiving means detects the front end as a reference point of counting, according to the value of the predetermined amount from the reference point and resultant value calculated by the operating means in order to select an effective portion out of the reflected light signal obtained via said light receiving means.

The nature, principle and utility of the invention will become more apparent from the following detailed description when read in conjunction with the accompanying drawings.

DESCRIPTION OF THE PREFERRED EMBODIMENTS

Embodiments of this invention will be explained hereinafter according to the attached drawings.

Figure 1:
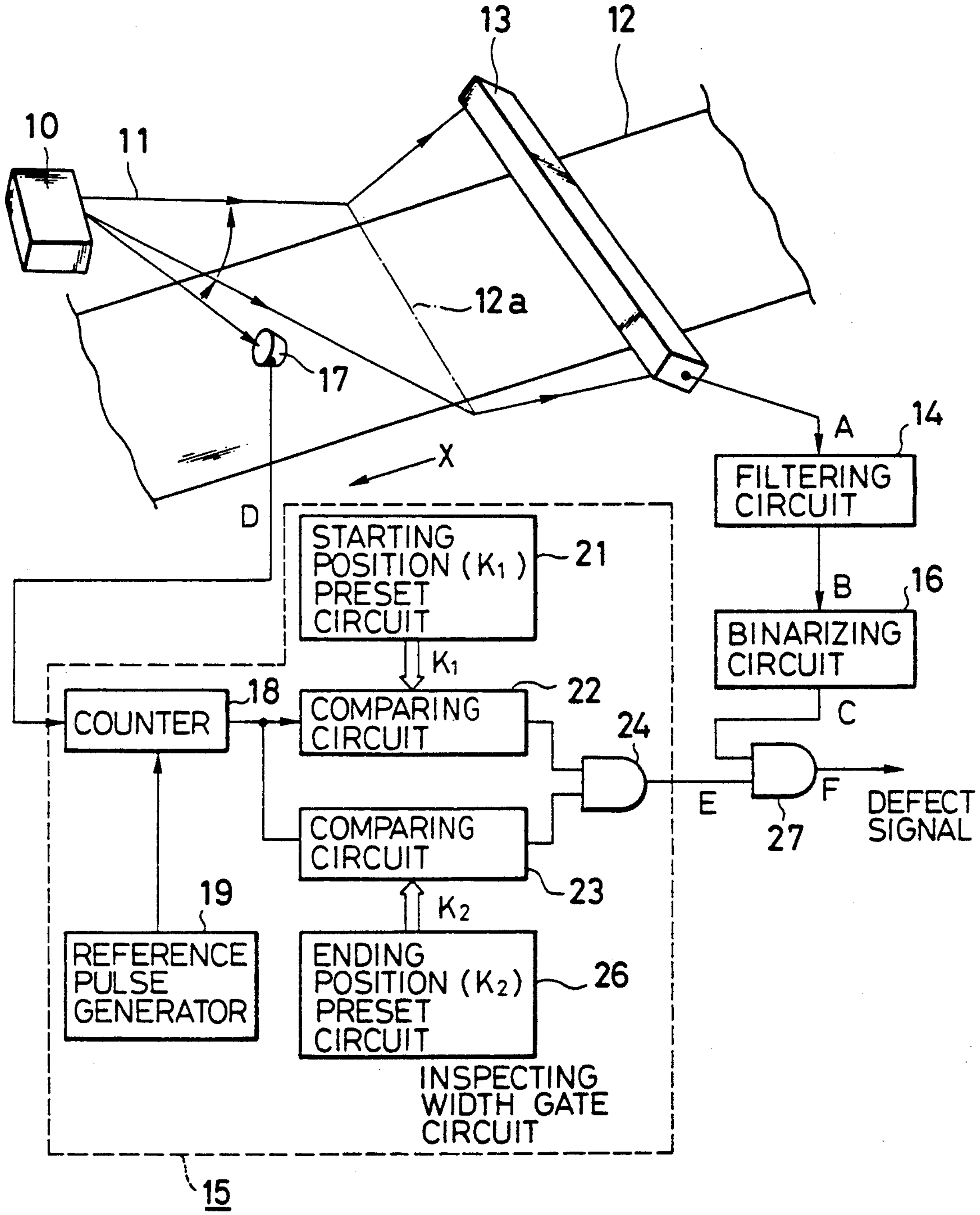
FIG. 1 shows the conventional surface inspecting apparatus.
Figures 2A, 2B, 2C, 2D, 2E, 2F:
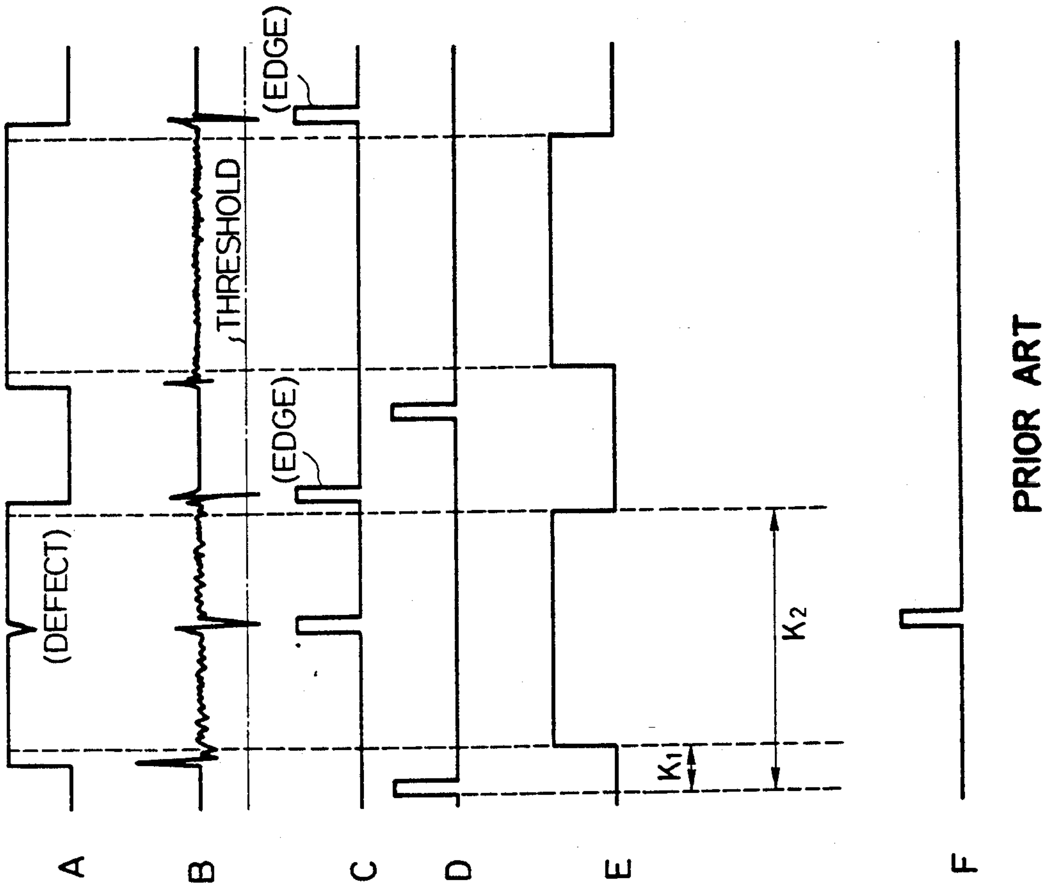
FIGS. 2A, 2B, 2C, 2D, 2E, and 2F are charts showing signal waves at the respective outputs of the main sections corresponding to FIG. 1.
Figure 3:
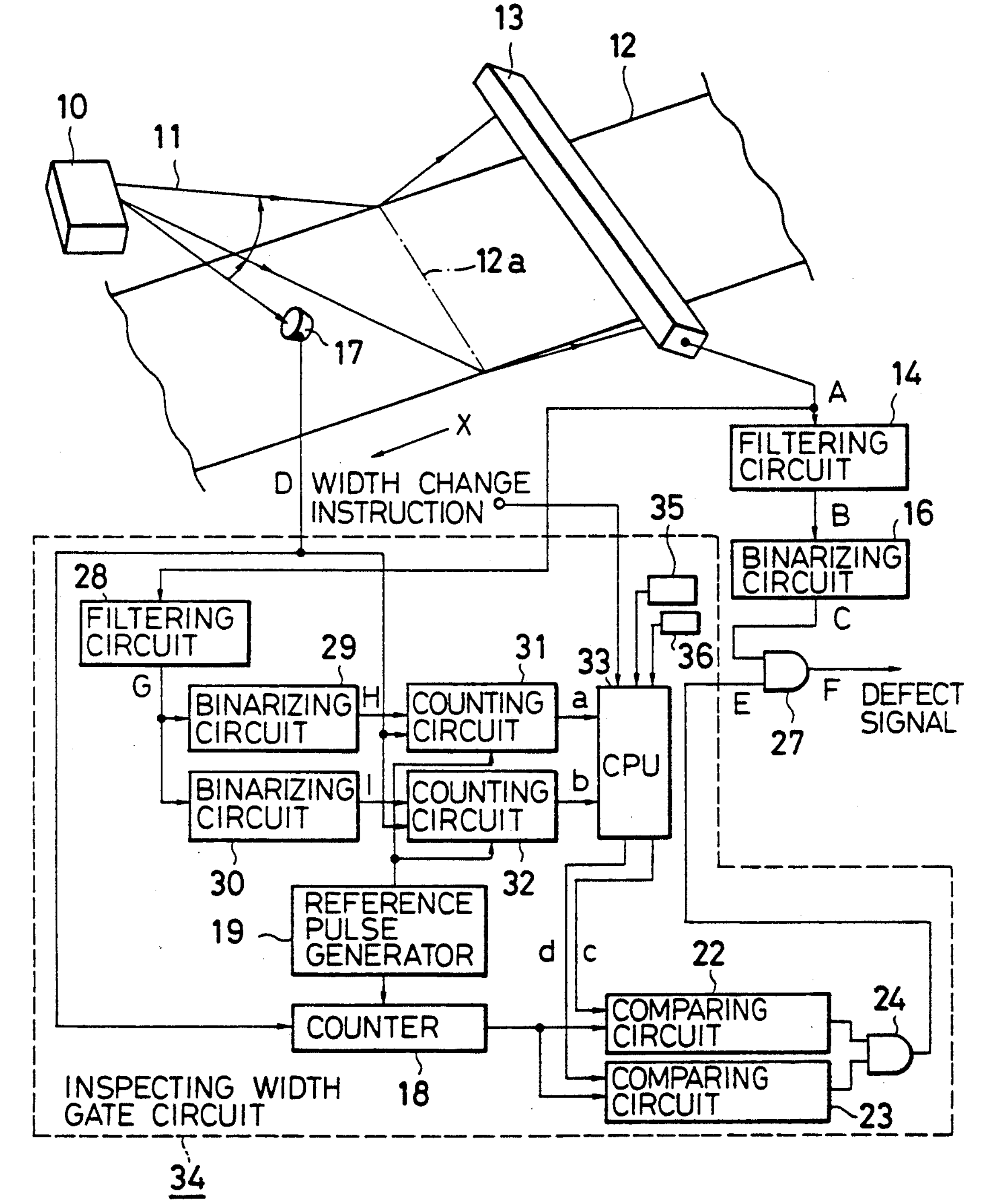
FIG. 3 is a schematic view of a first embodiment of the surface inspecting apparatus according to this invention.

FIG. 3 shows a block diagram explaining main sections in a first embodiment of the surface inspecting apparatus according to this invention. FIGS. 4A to 4H show output signals of the waveforms corresponding to their respective portions in FIG. 3.

Figures 4A, 4B, 4C, 4D, 4E, 4F, 4G, 4H:
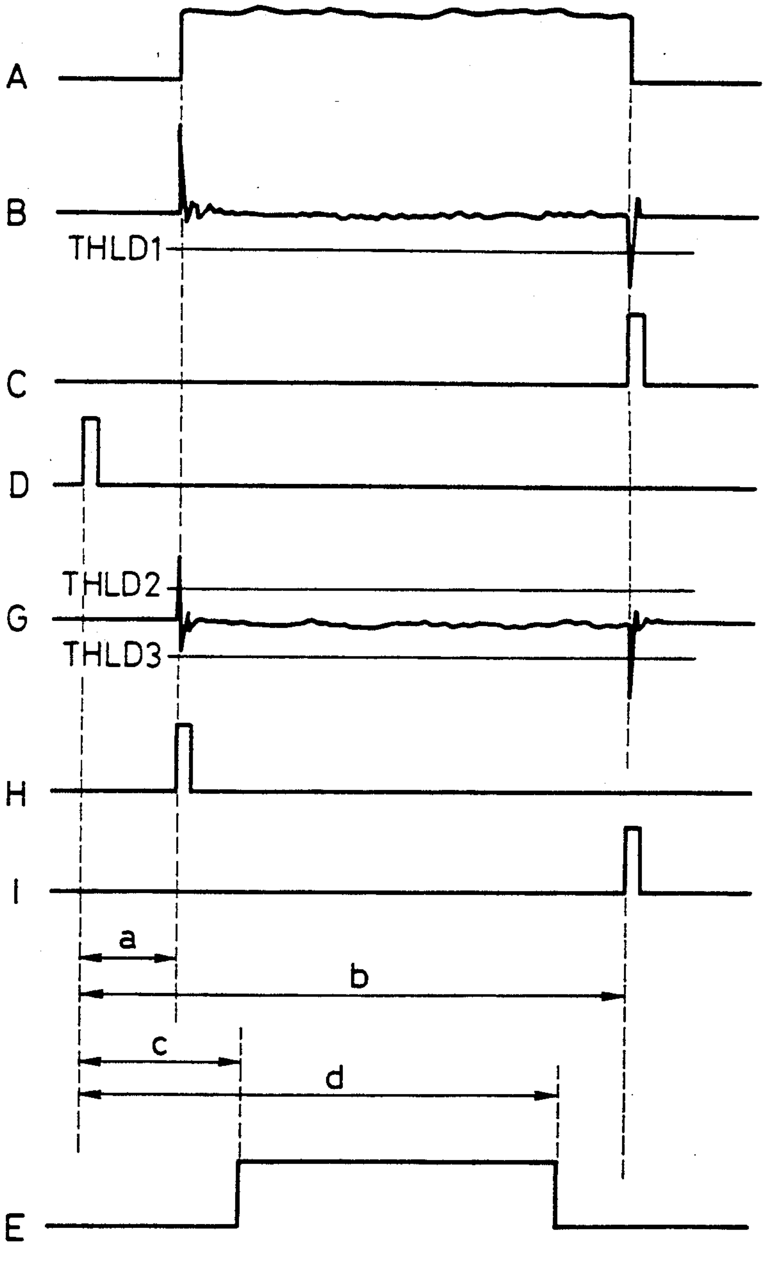
FIGS. 4A, 4B, 4C, 4D, 4E, 4F, 4G, and 4H are charts showing signal waves at the respective outputs of the main sections corresponding to FIG. 3.

A scanning light beam which is irradiated from a scanner 10 traces a scanning line 12*a* on the surface of a subject matter 12 moving in an X-direction. After being reflected in the position of the scanning line 12*a*, the light beam 11 enters a light detector 13, to be photoelectrically converted. The electric signal A as shown in FIG. 4A outputed from the light detector 13 is subjected to the waveform shaping in a filtering circuit 14 so as to clearly show a portion having a defect. The filtered signal B is classified into what exceed a threshold level THLD1 and otherwise by means of a binarizing circuit 16, for example as shown in FIG. 4B, the signal B over the threshold level THLD1 is allotted to "1" as a defect signal and the signal B under the threshold level THLD1 is allotted to "0" as a normal signal. The process described up to here is similar to the conventional method.

Now, the signal C as shown in FIG. 4C outputted from the binarizing circuit 16 is inputted into an AND circuit 27 together with a signal E as shown in FIG. 4H transmitted from an inspecting width gate circuit 34. As a result as long as the signal E is effective, the signal C is outputted from the AND circuit 27 as a defect signal F. Here, the signal E obtained from the inspecting width gate circuit 34 is generated as explained hereinafter. First, the electric signal A from the light detector 13 is inputted also into another filtering circuit 28, to an output signal G as shown in FIG. 4E. The output signal G then is inputted into a binarizing circuit 29 on the starting side as well as another binarizing circuit 30 on the ending side. The binarizing circuit 29 has a positively polarized threshold THLD2 and binarizes the inputted signal G to output a signal H as shown in FIG. 4F, while the binarizing circuit 30 has a negatively polarized threshold THLD3 and then binarizes the same inputted signal G to output a signal I as shown in FIG. 4G. A counting circuit 31 on the starting side is caused to count the number of the reference pulses sent from a reference pulse generator 19 (for example 10 MHz clock) as soon as a laser scanning timing detection signal D is inputted and keeps on counting until a pulse signal on the signal H. A CPU (Central Processing Unit) 33 acquires the information as to the reference pulse number a counted, as explained above, by the counting circuit 31 on the starting side during the interval between the detecting pulse signal on the signal D and the pulse signal on the signal H. In the same manner, the counting circuit 32 on the ending side counts the number of the reference pulse generated by the reference pulse generator 19 from the detecting pulse signal on the signal D to the pulse signal on the signal I, then the information on the reference pulse number b is read by the CPU 33.

After the above process, a value c being a little bit larger than the reference pulse number a is prepared therefrom to be set in a comparing circuit 22 as well as a value d being a little bit smaller than the reference pulse number b is prepared therefrom to be set in another comparing circuit 23. On the other hand, a counter 18 counts the number of the reference pulse transmitted from the reference pulse generator 19 by taking the detecting pulse signal on the signal D as the starting point, and provides the count information to the comparing circuits 22 and 23. In this situation, the comparing circuit 22 operates in such a manner that the signal outputted therefrom is kept at a low level as long as the number of the reference pulses from the counter 18 is smaller than the set value c, and then changes over from the low level to a high level when the number of the reference pulses becomes larger than the set value c. In a similar manner, the signal outputted from the comparing circuit 23 is kept at a high level while the number of the reference pulse from the counter 18 is smaller than to the set value d and changes over from the high level to the low level when the number of the reference pulses exceeds the set value d. The outputs thus operated are inputted into the AND circuit 24, which alternatively outputs a signal E as shown FIG. 4H.

It is only when a width change instruction from without is inputted that the CPU 33 reads the count numbers a and b to reset the values c and d. That is, the signal indicating that the width change of the subject matter has been performed must be given, for example, by a host computer. On this occasion, the CPU 33 is adapted to detect the starting position as well as the ending position, as above-described, by automatically detecting the edges with the light receiver 13.

Figure 5:
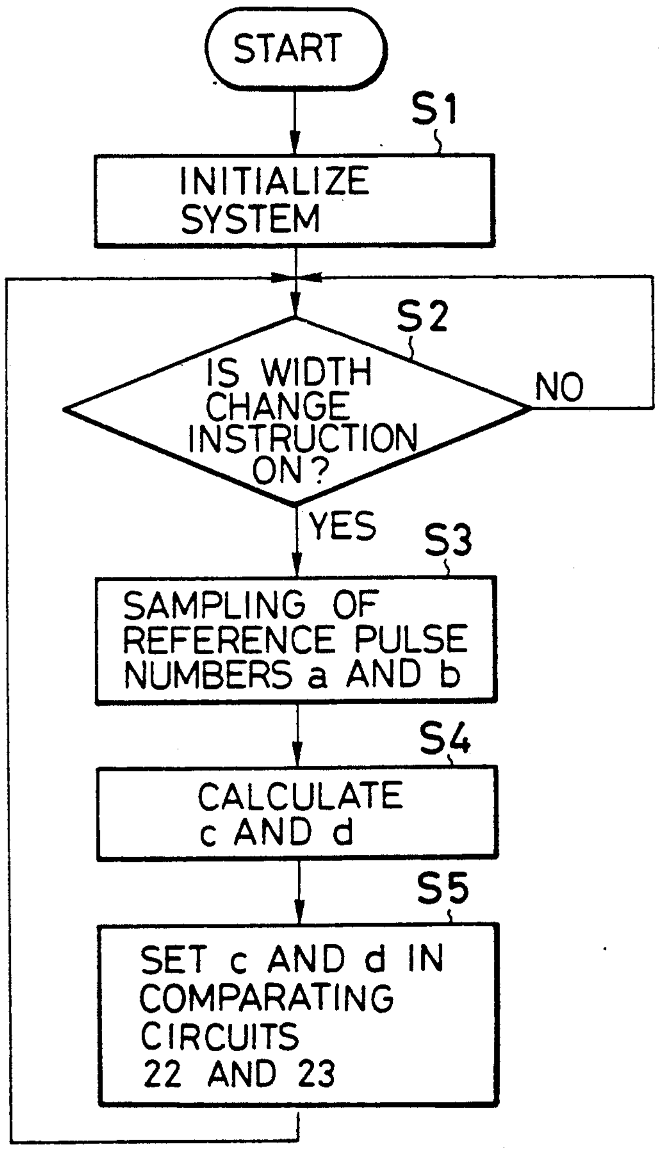
FIG. 5 is a flow chart showing an operation of the CPU 33.

FIG. 5 shows an operational flow chart of the CPU 33, in which first the system is initialized (Step S1) and the judgement of whether the width change instruction is on or not (Step S2). When the width change instruction is on, the sampling of the reference pulse numbers a and b are repeatedly effected up to a designated sampling frequency n and at designated intervals (Step S3). Then, in accordance with n values of the reference pulse number a obtained in the n times sampling, the average of the values with the minimum value and the maximum value being rejected among them is found out in order to calculate the value c being a little bit larger than the average. Again in the similar way, a average of the values with the minimum value and the maximum value being rejected in accordance with n values of the reference pulse number b, is found out to calculate the value d which is a little bit smaller than the average (Step S4). Thus obtained values c and d are set into the comparing circuits 22 and 23 respectively (Step S5). It is noted that the sampling frequency and the sampling interval are adapted to set by means of a sampling frequency preset circuit 35 and a sampling interval preset circuit 36, respectively.

Figure 6:
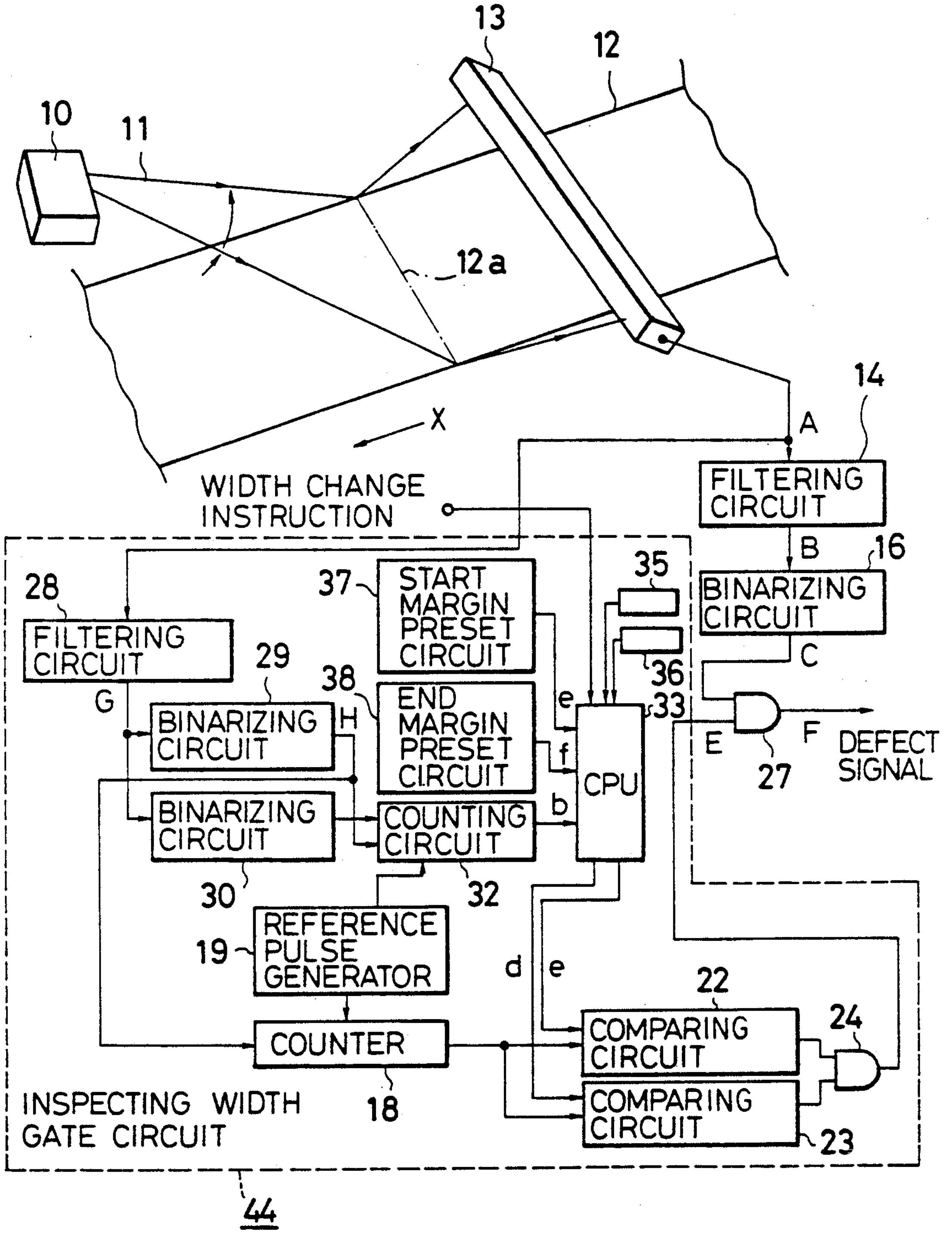
FIG. 6 is a schematic view showing a second embodiment of the surface inspecting apparatus according to this invention.

FIG. 6 shows another block diagram explaining main sections in a second embodiment of the surface inspecting apparatus according to this invention. FIGS. 7A to 7G show output signals of the waveforms corresponding to respective portions in FIG. 6.

Figures 7A, 7B, 7C, 7D, 7E, 7F, 7G:
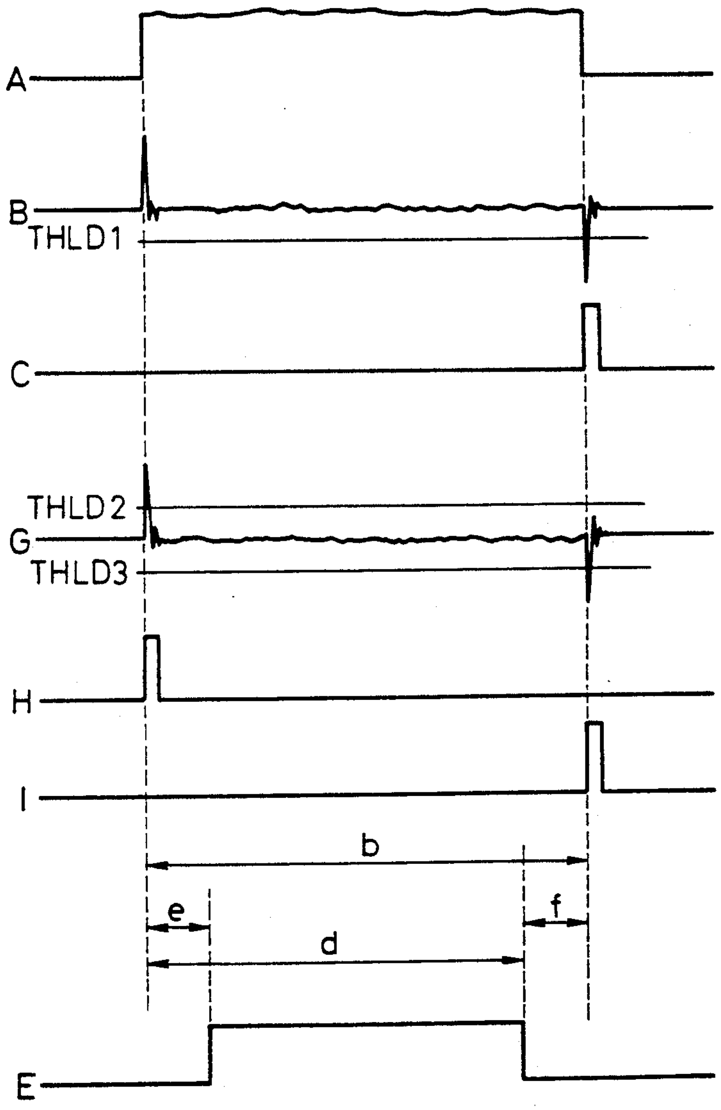
FIGS. 7A, 7B, 7C, 7D, 7E, 7F, and 7G are charts showing signal waves at the respective outputs of the main sections corresponding to FIG. 6.

Hereinafter, the explanation of the second embodiment will be described referring to FIG. 6 and FIGS. 7A to 7G so as not to overlap the explanation of the first embodiment. In the second embodiment, since the photosensor 17 as used in the first embodiment is removed, the rising pulse signal H on the starting side as shown in FIG. 7E prepared from the signal A obtained via the light detector 13 is adopted as a reference position instead of the signal D. In this case, there is no need to count the number a in the first embodiment, so that the counting circuit 31 on the starting side is unnecessary. According to this configuration, it is possible to follow up the ends of the subject matter 12 for matching the inspecting width whenever the subject matter 12 progresses rolling from side to side to some extent. In addition, a value e equivalent to "a little bit" of "a value being a little bit larger than the number a" expressed in the first embodiment can be set by means of a switch of a start margin preset circuit 37 newly added as well as a value f equivalent to "a little bit" of "a value being a little bit smaller than the number b" can be set by means of another switch of an end margin preset circuit 38 added. In this way, the CPU 33 sets the value e itself in the comparing circuit 22 while setting a value d in the comparing circuit 23 by operating $d=b-f$. Adding these preset circuits 37 and 38 allows the apparatus to freely set and reset the range of an unused area.

Figure 8:
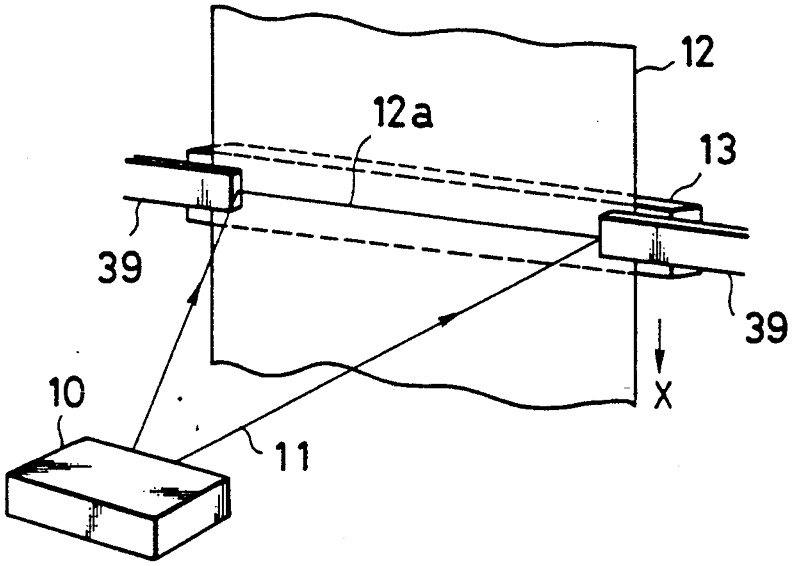
FIG. 8 is a schematic view showing a third embodiment of the surface inspecting apparatus according to this invention.

FIG. 8 is a schematic view for explaining a third embodiment of the surface inspecting apparatus according to this invention. When an inspection is carried out by a transmission type or a reflection type on a roll, it may disadvantageously happens that the rise signal and the fall signal are not detected clearly. The embodiment as shown in FIG. 8 is provided to compensate for the defect by shading the light at both ends by means of shading plates 39,39, which are adapted to automatically follow the respective edges of the subject matter 12. Consequently, the distance between the plates is adapted to change in accordance with the change of the width, thus automatically following the inspecting width.

According to the surface inspecting apparatus of this invention, since even in a case that the width of the subject matter is changed, the effective inspecting width can be automatically set by merely inputting some signals from outside or the like, there is no need to manually reset whenever a subject matter is replaced by another, and it is also possible to prevent the mistake in setting, thus making it possible to perform inspecting exactly.

In addition, since the effective inspecting width is determined in such a manner buy taking the average of a plurality of sampling values from which the minimum value and the maximum value are rejected, it is possible to prevent against the mistake in measuring the width which is liable to be made by the real defect and the like, thus making it possible to set the effective inspecting width more reliably.

It should be understood that many modifications and adaptations of the invention will become apparent to those skilled in the art and it is intended to encompass such obvious modifications and changes in the scope of the claims appended hereto.

What is claimed is:

1. A surface inspecting apparatus wherein a subject having a front end and a rear end is inspected for detecting defects on a surface thereof by means of a scanner scanning and irradiating a light beam on said subject while said subject is being conveyed, said apparatus comprising: light detecting means for detecting said light beam before the starting of every scan; light receiving means for receiving light reflected from said subject; first counting means for making a first count during an interval from when said light detecting means detects said light beam until said light receiving means detects the front end of said subject; second counting means for making a second count in an interval from when said light detecting means detects said light beam until said light receiving means detects the rear end of said subject; operating means for calculating a first value which is larger than the first count counted via said first counting means by a predetermined amount, as well as a second value which is smaller than the second count counted via said second counting means by a predetermined amount; and gate signal generating means for generating a gate signal in accordance with the first and second values in order to select an effective portion out of the reflected light obtained via said light receiving means.

2. A surface inspecting apparatus as claimed in claim 1, wherein said light receiving means comprises means for detecting the front end and the rear end of said subject.

3. A surface inspecting apparatus as claimed in claim 1, wherein said apparatus comprises a reference pulse generating circuit for generating reference pulses, and wherein said first and second counting means count the reference pulses.

4. A surface inspecting apparatus as claimed in claim 1, wherein said first counting means is adapted to make a plurality of first counts and said second counting means is adapted to make a plurality of second counts, and wherein said operating means produces the first and second counts which are used to produce the first and second values, respectively, by averaging the plurality of the first and second counts with minimum and maximum counts being excluded, respectively.

5. A surface inspecting apparatus as claimed in claim 1, wherein said apparatus further comprises shading means for shading the light beam at both ends of said subject matter, and for controlling means for allowing said shading means to control the extent of shading based on the effective portion selected.

6. A surface inspecting apparatus as claimed in claim 1, wherein a reference point is determined when said light detecting means detects said light beam, and said gate signal generating means generates the gate signal from the reference point in accordance with the first and second values.

7. A surface inspecting apparatus as claimed in claim 1, wherein said apparatus comprises first storage means for storing the first value, and second storage means for storing the second value.

8. A surface inspecting apparatus wherein a subject having a front end and a rear end is inspected for detecting defects on a surface thereof by means of a scanner scanning and irradiating a light beam on said subject while said subject is being conveyed, said apparatus comprising: light detecting means for detecting said light beam before the starting of every scan; light receiving means for receiving light reflected from said subject; counting means for making a count during an interval from when said light receiving means detects the front end of said subject until said light receiving means detects the rear end of said subject; operating means for calculating a value which is smaller than the value counted via said counting means by a first predetermined amount; and gate signal generating means for generating a gate signal according to a second predetermined amount from the the front end detected by said light receiving means and the value calculated by said operating means in order to select an effective portion out of the reflected light obtained via said light receiving means.

9. A surface inspecting apparatus as claimed in claim 8, wherein said apparatus further comprises shading means for shading the light beam at both ends of said subject, and controlling means for allowing said shading means to control the extent of shading based on the effective portion selected.

10. A surface inspecting apparatus as claimed in claim 8, wherein said apparatus comprises first storage means for storing the value calculated by said operating means.

* * * * *